United States Patent [19]

Landwehr

[11] Patent Number: 4,786,925
[45] Date of Patent: Nov. 22, 1988

[54] PHOTOGRAPHIC CONTOUR MEASUREMENT

[76] Inventor: Ulrich M. Landwehr, Bahnhofstrasse 8, D-3000 Hannover 1, Fed. Rep. of Germany

[21] Appl. No.: 67,930

[22] Filed: Jun. 29, 1987

[30] Foreign Application Priority Data

Jun. 30, 1986 [DE] Fed. Rep. of Germany ....... 3621927

[51] Int. Cl.⁴ ...................... G03B 15/00; G03B 29/00; G03B 21/26; G01B 11/28
[52] U.S. Cl. ......................................... 354/77; 354/62; 354/290; 353/28; 353/30; 353/40; 353/94; 356/376; 356/379
[58] Field of Search ..................................... 354/75–78, 354/62, 290; 353/28, 30, 40, 41, 94; 250/237 G; 356/376, 379

[56] References Cited

U.S. PATENT DOCUMENTS

| | | | |
|---|---|---|---|
| 3,749,484 | 7/1973 | Busche | 353/94 |
| 4,370,039 | 1/1983 | Landwehr | 354/77 |
| 4,535,782 | 8/1985 | Zoltan | 356/379 X |
| 4,564,295 | 1/1986 | Halioua | 250/237 G X |
| 4,639,107 | 1/1987 | Landwehr | 354/77 |

FOREIGN PATENT DOCUMENTS 2246909  4/1974  Fed. Rep. of Germany ........ 354/77

Primary Examiner—W. B. Perkey
Attorney, Agent, or Firm—Ralf H. Siegemund

[57] ABSTRACT

Horizontal lines are projected onto a person from a plurality of overhead projectors, each projecting at a 45 degrees angle, all of the projectors have parallel optical axes, the person being photographed with the projected raster superimposed.

8 Claims, 2 Drawing Sheets

PHOTOGRAPHIC CONTOUR MEASUREMENT

BACKGROUND OF THE INVENTION

The present invention relates to the ascertainment of dimensions, measurements, topology, surface contour and the like of three dimensional object such as a person under utilization of photography, and more particularly the invention relates to ascertaining body size and contours of a human being by means of photography whereby the person is photographed together with a measuring line raster, in that upon taking of the picture or plurality of pictures a line raster pattern is projected onto the body or object.

A method of the kind to which the invention pertains is disclosed and shown for example in German Pat. No. 29 48 010 corresponding to my U.S. Pat. No. 4,370,039 and German printed patent application No. 34 25 913 corresponding to my U.S. Pat. No. 4,639,107. The line raster as projected from above permits in fact the introduction of 3-dimensional aspects. Whenever the lines as projected onto the object or body deviate from the horizontal (assuming the lines as projected are horizontal) then these lines are distorted and in fact delineate as far as there is a deviation from the horizontal is concerned, a third dimensional contour. For instance, if a horizontal line is projected from above and the projected line deflects upwards, this represents a physical projection of the object towards the camera. If the line raster is sufficiently tight i.e. exhibiting a significant resolution then one can in fact establish a fairly detailed 3-dimensional topological picture of the surface of the object facing the camera. The line raster for example is produced in accordance with the known method by means of a flash projector and a slide for the line pattern. There is, however, a disadvantage when the body is tall and in close-up photography the human body is in fact such a large body. One may not be able to cover the entire body in one picture but has to show at least the torso of the person. In this case all lines except the line that is projected at a 45 degrees angle will have to be subjected to different conversions in order to extract exact physical measurements from the photograph.

DESCRIPTION OF THE INVENTION

It is an object of the present invention to improve my known methods in such a manner that the corrective calculation and computations can be dispensed with without compromising the accuracy of the measuring result.

It is a particular object of the present invention to provide a new and improved method and equipment ascertaining topological (surface contour dimensional) measurements of an object such as the human being, under utilization of photography as well as by projection of a horizontal line raster from above onto that object or a human being.

In accordance with the preferred embodiment of the present invention it is suggested to produce (project) a line raster under utilization of a plurality of vertically stacked light sources (projectors) whose optical axes all run at the same angle, preferably of nearly 45 degrees, to the vertical; the projector being very narrow in the vertical. The inventive features produce very small deviations of the individual lines as projected from the optical axis at the angle of 45 degrees. The deviation is so small that there is no noticeable distortion in the result. Of particular advantage is to provide the individual lines at equidistant spacing of a slide being projected and owing to the multiple projection the line rasters will be equidistantly spaced throughout. The light sources producing the line raster are preferably arranged one above each other, each having its own slide with a line pattern that is being projected. They are preferably flash projectors mounted on a common carrier which is inclined to the vertical. The projectors have to be arranged physically between the object to be photographed and the camera, but above the axis of the camera so that the field of view of the camera is not obscured. The inclination of the carrier makes sure that even if the flash projector assembly occupies a fairly large amount of space in the vertical direction they will not appear as such in the picture. The light sources (projectors) are preferably fixed for example in the corner of the room. The projected raster plane i.e. the place and plane where the object to be measured is to be placed are projected movably in the horizontal. This way one can for example use a raster of about 1 m height which is sufficient for measuring the torso of small as well as large persons.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Figure 1:
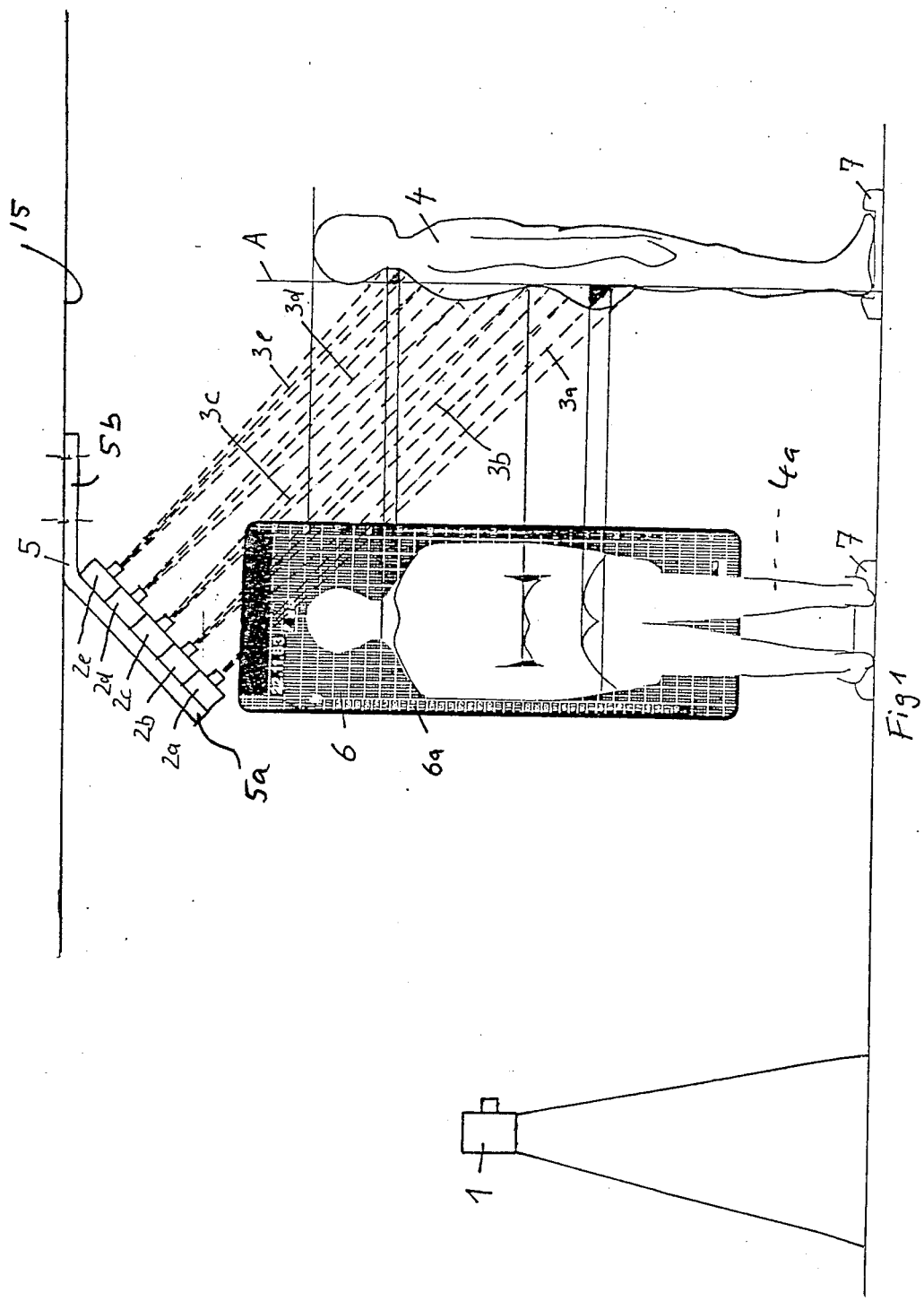
FIG. 1 is a side elevation of a device in accordance with the preferred embodiment of the present invention for practicing the best mode thereof by the image of the object to be photographed as shown offset to the left.

Proceeding to the detailed description of the drawings it is seen that ref. numeral 1 refers to a self developing "instant" type camera; flash projectors 2a,b,c,d, and e are provided overhead above the camera are well as the stage that is being photographed right hand side of FIG. 1 each projector projects a slide with line rasters so that there are projection bundles 3a,b,c,d,e which reach the person 4. The person being photographed is assumed to stand on a stand 7 constructed as a balancing scale as shown in German patent application No. 33 01 864. This scale provides for an indication (and therefore a representation towards correction) of the posture of the person 4.

The fan out of the projection beams at each instance is not very great in the vertical so that basically the projection rays are at 45 degrees to the vertical with very little deviation from that angle. Moreover, the projectors are equidistantly spaced so that owing to the parallelism of the optical axes to each other, these axes are equidistantly projected e.g. onto a vertical projection plane (e.g. A). If a horizontal raster line runs in each instance through the optical axis, then these horizontal lines are equidistantly projected into plane A.

The projectors are arranged on a carrier 5 which has an oblique arm 5a and a top portion 5b by means of which the carrier as a whole is fastened to the ceiling 15 of the room. That part of the carrier namely 5a on which are fastened the five projectors 2a–2e, is arranged at a 45 degree angle to the ceiling so that its end ever for relatively low rooms will positively not reach the range of camera 1.

Each one of the projectors 2a–2e is fastened to the carrier 5 (arm 5a) so that, as stated, the optical axis in each instance has exactly an angle of 45 degrees to the vertical (or to the horizontal). That particular angle is exemplary only but clearly preferred because no correction is needed to translate vertical deflectors (in a vertical plane) into horizontal (topological) dimensions because the tangent of 45 degrees is unity. The accuracy of measurement is of course the higher the more lines one projects. Thus, it is of advantage to provide a distance of the lines as projected to be about 2 cm. Assuming that the torso to be imaged i.e. its vertical dimensions are to be covered by a single photograph, one needs about 50 lines if the five flash light projectors 2a–2e each project about 10 lines per projector. The number of lines should not larger since a larger number of lines means a larger fan out for each of the beams which in turn means an upper and lower edge zones in which the deviations from the 45 degrees angle may begin to increase noticeably.

Figure 2:
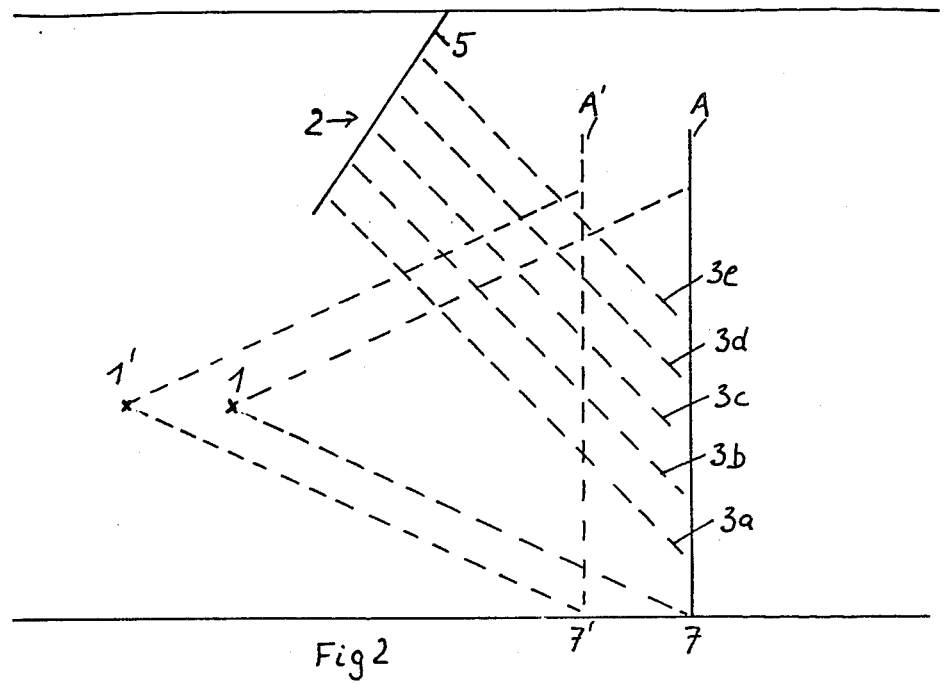
FIG. 2 illustrates the ray path with details relevant for the device shown in FIG. 1.

FIG. 2 illustrates the ray path in relation to camera 1 as well as in relation to the flash projector assembly 2. By sliding camera 1 as well as the balancing scale 7 in horizontal direction the height of the raster as projected can be shifted up or down. This means that a measuring area covering only 1 m height one can measure tall and small people over the entire focal length.

FIG. 1 shows also a measuring raster 6 and in a front view. This background raster is preferably projected from the side into the picture by way of double exposure as disclosed in my U.S. Pat. No. 4,639,107. Hence, the measuring raster is superimposed upon the object plane A just for purposes of reference, the human FIG. 4a is shown superimposed upon this measuring raster and as it appears in the camera. The raster 6 can be understood to be affixed to a side walls and owing to a semitransparent mirror in the ray pattern (see FIG. 2 of U.S. Pat. No. 4,639,107) the camera sees this raster 6 and the person 4a, the latter as shown in the superimposed relationship.

Next to the position of the person to be measured is provided a ruler 6a with number and elevational markings and white panel areas. This establishes the raster plane as the reference plane for the three dimensional measurement on the photo. It is necessary to provide for a situation in that the person whose body topology is subject to measurement, is in a still and resting position. For this a comfortable position must be established which is the purpose of the balancing scale 7.

The frontal view of the person, 4a, shows certain corresponding lines as far as the projection of horizontal lines is concerned and one can see that the up or down distortion of the projected lines, owing to the body contour, establishes very clearly how the raster as projected is distorted in representation of the body bulges and indents extending basically towards and away from the camera.

Figure 3:
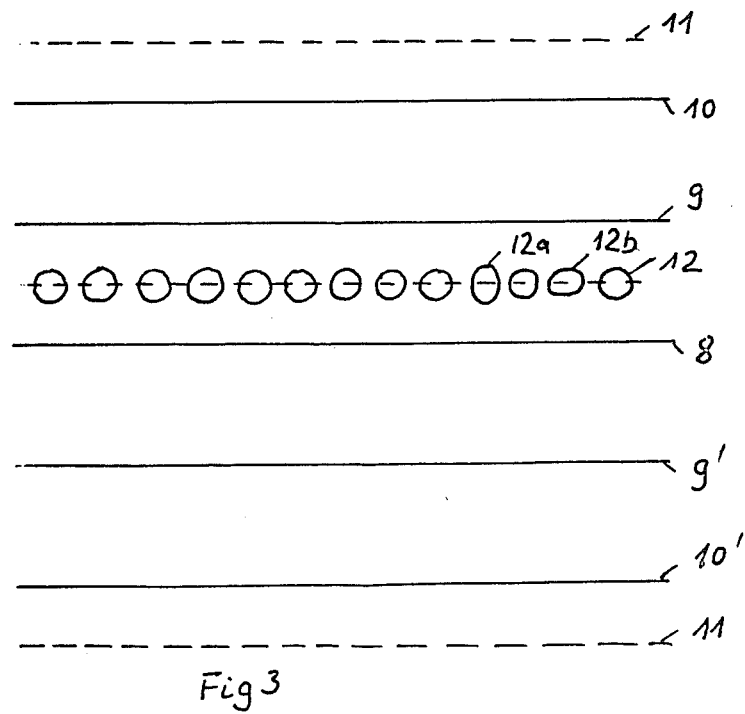
FIG. 3 is a front elevation of the line raster of a single flash light projector.

FIG. 3 illustrates a line raster of a single flash light projector i.e. as projected by one of the projectors 2a–2e. Here it is assumed that just five lines are being projected. If one projector covers 10 cm then in this case ten rather than five projectors are required if the line spacing is 2 cm as before. The middle line 8 (e.g. the center) is traversed by the optical axis or the respective projector. Deviations of the projected lines 9 and 10 and 9' and 10' in relation to the 45 degrees angle is so small that they do not have to be considered in ascertaining the desired measuring values. The dotted line 11 extends in the border region between two adjacent line rasters. Between the lines 8 and 9, for instance, one may include in the projection some symbols such as circles 12, the reason for this is that small deformations can now also be recognized because as shown the circles will locally be slightly eliptically deformed such as circles 12 and 12b.

The invention is not limited to the embodiments described above but all changes and modifications thereof, not constituting departures from the spirit and scope of the invention, are intended to be included.

I claim:

1. In an imaging method for ascertaining the dimensions of an object by means of photography using a camera and including the step of projecting during imaging and in an oblique direction a particular pattern of horizontal lines upon the object to be imaged, the improvement comprising:
   using a plurality of narrow bundled projection beams arranged one above each other each with an optical axis of about 45 degrees to the vertical and each projecting a relatively small plurality of horizontal lines upon said object.

2. Method as in claim 1, wherein the projectors are such that horizontal lines traversed by the respective optical axis of projection, are equidistantly projected in a vertical projection plane oriented towards the camera.

3. Method as in claim 1 wherein the horizontal lines as projected are all equidistantly spaced.

4. Method as in claim 1 including adjusting the camera and a stand of the object together in horizontal direction to thereby shift the lines as projected up or down.

5. Apparatus for acquiring the topological dimensions of an object by means of a photographic camera and comprising in addition a plurality of projectors arranged one above the other overhead above said camera, each projector projecting a horizontal line pattern upon said object, each of the projectors having an optical axis such as parallel to the respective other axes, said axes each having an angle of 45 degrees to the vertical.

6. Apparatus as in claim 5 said projectors being affixed to a common carrier extending to the respective rear end thereof.

7. Apparatus as in claim 6 said carrier having an oblique arm on which said projectors are affixed.

8. Apparatus as in claim 5, the camera being slidable along its optical axis

* * * * *